March 23, 1937. J. C. RASMUSSEN Plant Pat. 239
CARNATION
Filed Sept. 14, 1936
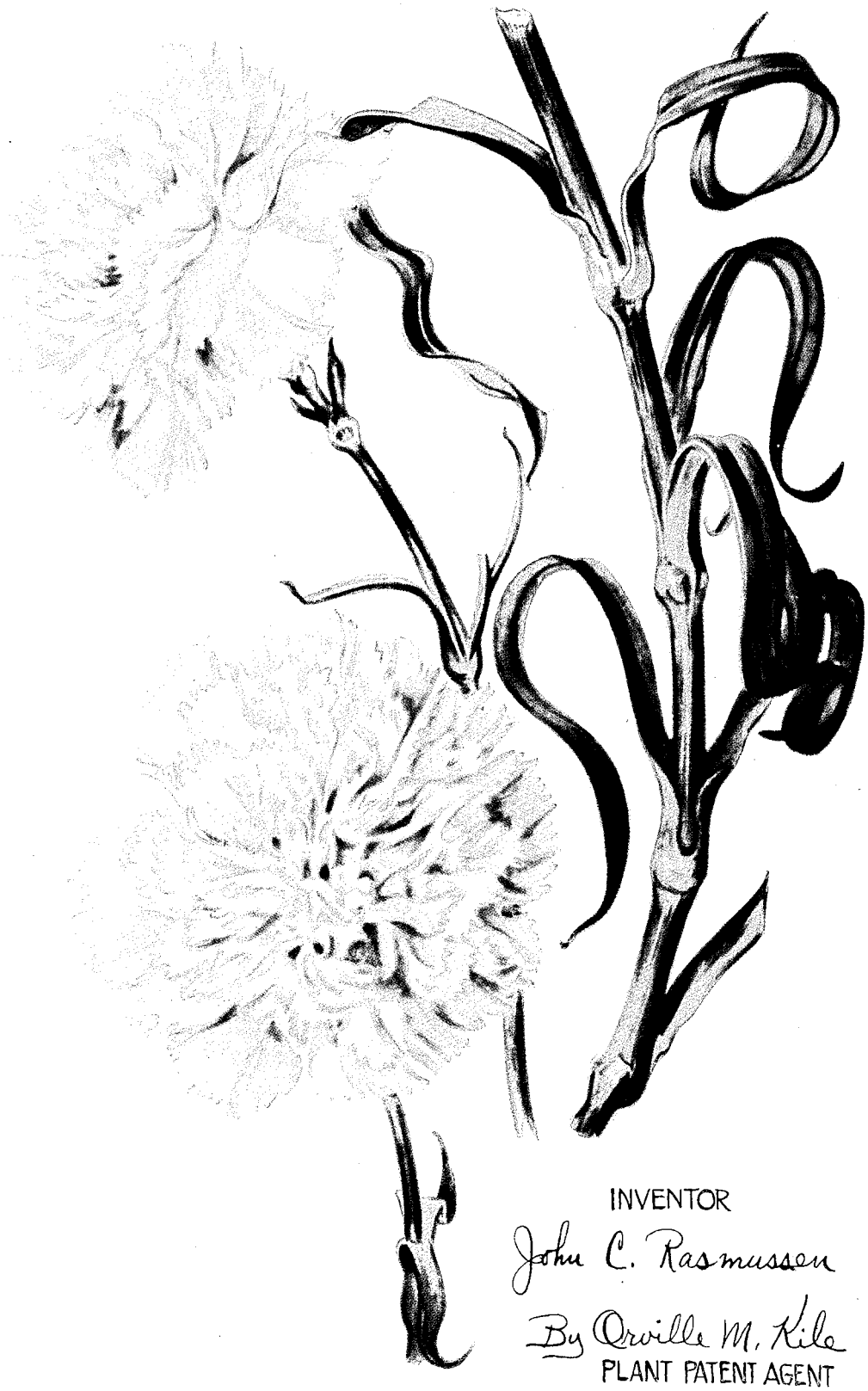
INVENTOR
John C. Rasmussen
By Orville M. Kile
PLANT PATENT AGENT Patented Mar. 23, 1937

Plant Pat. 239

UNITED STATES PATENT OFFICE

239

CARNATION

John C. Rasmussen, New Albany, Ind., assignor to Louis Alfred Kintzele, Denver, Colo.

Application September 14, 1936, Serial No. 100,766

1 Claim. (Cl. 47—60)

My present invention relates to improvements in fragrant carnations of the type known as perpetual blooming or greenhouse forcing carnations. The object of my invention is to provide a new and improved deep rose carnation of the type mentioned, having blossoms of a distinctive and pleasing color, unusually large size, heavy petalage, regular form and good lasting qualities; also having long and strong stems and a tough calyx which seldom splits, as well as other desirable qualities.

My new variety of carnation is the result of a cross between the varieties Laddie and Early Rose, followed by careful re-selection.

The original illustrations show in full color two views of the flower and a portion of the lower end of the stem of this new variety of carnation.

The following is a detailed description of the carnation and all color references are to Ridgway's Color Standards and Nomenclature.

*The plant*

This plant is a very vigorous grower, attaining a height of 3 to 3½ feet, and is apparently resistant to diseases which usually affect carnations. There are few side shoots and no "grassiness". A single plant will produce 15 or more large blooms per season after pinching.

*Stems.*—Very long, measuring 35 to 40 inches in length. Stiff and strong; large at base (typical specimens measure ⅜ inch in diameter at the base).

*Color.*—Elm Green (Plate XVII), slightly overlaid with gray bloom.

*Nodes.*—Large, many at base of stem measuring one-half inch or more in diameter.

*Foliage.*—Long but not grassy; straight rather than curled.

*Color.*—Dark Dull Yellow-Green (Plate XXXII) overlaid with gray bloom.

*Calyx.*—Exceedingly tough and strong. Consists of single tube divided into five lobes.

*Size.*—Relatively short and wide—measures about 1¼ inches long and about the same in width.

*Bracts.*—Strong bracts; webbed together at base of calyx.

*The flower*

Bloom:—

*Color.*—Uniformly Tyrian Rose (Plate XII). The under side of the petal is somewhat lighter, approximately Rose Color (Plate XII). No white portions are found on the petals except the portion which is enclosed in the calyx.

*Petalage.*—An unusually large number of petals, averaging 80 to 90 (including all small ones) in the month of June. They are closely folded in the center of the flower, although not curled.

*Petals.*—Outer petals are large, measuring 1¾ inches in width and 1½ inches from top to claw or shank (total of 2½ inches from top of petal to bottom of shank). The central petals are much shorter and smaller than the outer petals. All petals are slightly serrated.

*Texture.*—Heavy and durable.

*Fragrance.*—Pleasing; moderate.

*Size.*—Very large—measuring from 3½ to 4½ inches across.

*Shape.*—Regular; almost perfectly round, with flattened center, increasing the impression of great width of the flower.

*Longevity.*—Keeping qualities as a cut flower exceptionally good (typical blossoms lasted a week after having been received in Washington, D. C. from Denver, Colorado).

Bud:—

In early stages, short and bulged. About two weeks before maturity the calyx lengthens.

*Reproductive organs*

*Stamens.*—Long; white. Fifteen to twenty in each flower.

*Anthers.*—Small; light yellow. Arise from pithy ring at base of ovary.

*Pistils.*—Three or four (sometimes two) very long pistils, measuring 2 inches in length. Large; white with pinkish tips; curved at end. Because of their great length they usually show slightly in the opened flower despite the large number of petals.

*Ovary.*—Five-lobed; very large and high, with many ovules. Set high on pithy knob enclosed in ring to which are attached the stamens surrounding the ovary.

Having thus disclosed my invention, what I claim as new is:

The carnation with qualities in combination as shown and described, characterized particularly by its blossoms of a distinctive Tyrian Rose color; its unusually large size and heavy petalage; its tough and strongly constructed calyx; its exceptionally long and strong stems; and its superior keeping qualities.

JOHN C. RASMUSSEN.